United States Patent [19]

Kakascik

[11] Patent Number: 5,467,657
[45] Date of Patent: Nov. 21, 1995

[54] METHOD AND DEVICE FOR CORE SAMPLING STEEL

[75] Inventor: Tim Kakascik, Wintersville, Ohio

[73] Assignee: Wheeling Pittsburgh Steel Corporation, Wheeling, W. Va.

[21] Appl. No.: 174,981

[22] Filed: Dec. 29, 1993

[51] Int. Cl.$^6$ .................................................. G01N 1/04
[52] U.S. Cl. ......................................................... 73/864.44
[58] Field of Search ............ 73/864.41, 864.43–864.45,
73/864.44; 225/1; 30/167, 168

[56] References Cited

U.S. PATENT DOCUMENTS

| | | | |
|---|---|---|---|
| 1,598,458 | 8/1926 | Sullivan | 30/168 |
| 2,634,775 | 4/1953 | Unsinger | 30/167 |
| 2,963,785 | 12/1960 | Dilling | 73/864.44 |

Primary Examiner—R. Raevis
Attorney, Agent, or Firm—Buchanan Ingersoll; Robert J. Pugh

[57] ABSTRACT

A method and apparatus for extracting a test sample from a metal object. An annular portion of metal is removed from the metal object, such that an annular cavity surrounds a cylindrical sample of metal. A tool having a rigid elongated shaft is provided. The shaft has a longitudinal axis and a first end and a second end. The first end of the shaft has a cylindrical lower surface and a cylindrical upper surface which lie at a selected angle relative to one another such that the first end of the shaft is tapered. The first end of the shaft terminates in an arcuate edge. The arcuate edge of the tool first end is then inserted into the annular cavity surrounding and forcibly engaging the cylindrical sample. A longitudinally-directed force is then administered upon the second end of the tool until the sample is separated from the object.

4 Claims, 2 Drawing Sheets

METHOD AND DEVICE FOR CORE SAMPLING STEEL

BACKGROUND OF THE INVENTION

1. Field of the Invention

This invention relates to extracting and obtaining samples of steel taken from a steel source.

2. Description of the Prior Art

Methods of continuously casting steel are known in which molten steel is delivered from a ladle through a vertical cooling device and is then feed horizontally as an elongated continuous length of steel. The metallurgical content of the steel is obtained by providing the appropriate mix of materials in the ladle. By altering the make up of these ingredients, the metallurgical content of the steel may be selectively altered.

When the metallurgical content of the steel is changed from one type to another type, one portion of the continuous length of steel has a first metallurgical content and another portion of the continuous length of steel has a different metallurgical content. Between the two metallurgically-different portions of steel, there is a transition period in which the steel has a metallurgical make-up different from either of the two steel portions. This type of steel may be considered hybrid, and when cut as a slab is called a hybrid slab. The hybrid slab of steel may have a nonhomogenous metallurgical make-up, so that the metallurgical content of the hybrid slab is not the same at one end of the slab as at the opposite end.

Although the metallurgical content of the hybrid slab does not have the desired metallurgical content of the portion of steel proceeding it or the desired metallurgical content of the portion following it, the hybrid slab may be utilized if its metallurgical content could be determined. Therefore, some testing means must be utilized to determine metallurgical content of the hybrid slab. The testing means should not be destructive of the slab and should waste as little of the steel slab as possible.

The continuous length of steel is cut, typically by a flame cutting torch, into respective slabs. Slabs are cut by torches, therefore, the ends of each slab may be metallurgically altered due to the heat and chemical reactions from the torches. Thus, it is highly desirable that the tool extract a steel sample beyond the torch affected area of the slab. The sample extraction means should also waste as little usable steel from the slab as possible.

In the past, circular saws were used in which a series of angled cuts at the end of the slab resulted in a pyramidical configured sample being removed. The saw had to cut the slab beyond the torch heated area of the slab. For testing purposes, the sample need be only an inch or so in thickness, however, the circular saw cuts along the entire arc of the saw blade. Thus, this technique resulted in the waste of a great deal of steel, and sometimes penetrates the slab beyond the depth of the sample resulting in further unnecessary waste.

Therefore, a method is needed for obtaining steel core samples in a manner that reduces waste in the steel slab.

SUMMARY OF THE INVENTION

Some of the embodiments provide a method and apparatus for removing a sample from a metal source (such as a slab) for the purpose of testing the metallurgical content of the sample.

To extract a sample, a hole cutting saw is employed. The hole saw may have a cylindrical blade. The cylindrical blade makes a cylindrical cut into the end of the steel slab, creating an annular kerf or cavity in the slab which surrounds the cylindrical sample. This initial cut results in the sample being attached to the slab in a plane generally along the back of the kerf.

A sample extracting tool is then utilized. The sample extracting tool has a rigid elongated shaft, a longitudinal axis running through the shaft and a first end and a second end. The shaft first end has a cylindrical, convex outer surface and a cylindrical, concave inner surface. The shaft first end is tapered such that the inner and outer cylindrical surfaces lie at a desired angle relative to one another and converge so as to terminate in a generally arcuate edge. Preferably, the edge is rounded or radiused. The second end of the shaft is sized and configured to receive an impact thereto.

The inner and outer cyliindrical surfaces each have a respective radius. In some preferred embodiments, the radius of the inner cylindrical surface is substantially the same as the radius of the outer cylindrical surface. The length of the shaft, the angle of taper between the upper and lower cylindrical surfaces, the thickness of the shaft and the radii of the inner and outer cylindrical surface may each be selected based upon the desired size of the sample to be extracted.

The arcuate edge of the tool is then inserted into the kerf. The inner, concave cylindrical surface lies adjacent the sample when the first end of the tool is inserted into the annular kerf. The radius of the concave inner cylindrical surface is greater than or equal to the radius of the sample, and is preferably slightly larger than the sample radius.

When an impact is administered to the second end of the shaft, the edge of the first end is driven deeper into the annular kerf. The tool is driven into the metal and the edge of the first end is forced toward the bottom of the kerf causing a buildup of stress along the bottom of the kerf. The stress buildup along the bottom of the kerf causes a fracture of the steel where the sample is attached to the slab. The sample, which is generally cylindrical, is detached from the slab along the stress fracture. Thus, a generally cylindrical sample is obtained, permitting testing of the steel beyond the flame altered area without creating unnecessary material waste. The sample is removed without penetrating the slab deeper than the length of the cylindrical sample removed.

The tool is preferably fabricated of steel. The inner cylindrical surface and the outer cylindrical surface may lie at any desired angle relative to one another, depending on the depth of the sample. For typical sample depths (around 1 inch) the inner and outer cylindrical surfaces preferably lie at an angle of generally between 15° and 40° relative to one another, with the preferred angle being about 25°.

Therefore, the sample-extracting tool removes a sample from the metal object while leaving the metal outside the kerf undisturbed.

Other objects and advantages of the invention will become apparent from a description of certain present preferred embodiments thereof shown in the drawings.

DETAILED DESCRIPTION OF THE PREFERRED EMBODIMENTS

Figure 1:
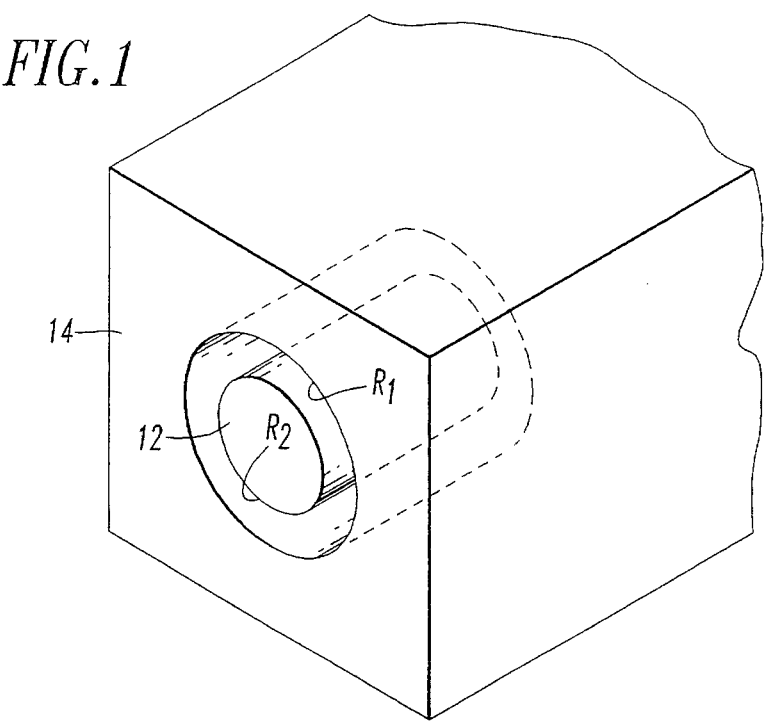
FIG. 1 is a perspective view of a steel slab having an annular kerf provided thereon, surrounding and defining a cylindrical sample.

Referring first to FIG. 1, a slab of metal 14 is shown, from which a sample is to be extracted. First, an annular section of the slab is removed from one face of the slab 14 leaving an annular kerf or cavity 16 extending into the face of the slab 14. The kerf 16 may be formed by any convenient means but is preferably formed through the use of a hole cutting saw (not shown) that preferably employs a cylindrical blade. The kerf 16 is provided into the face of the slab 14 at a desired depth at which the metallurgical qualities are to be examined. Typically, the slab is cut by a torch, thus, the kerf 16 is preferably disposed into the torch-cut face of the slab 14 at a depth beyond the flame-altered region of the end of the slab.

Once the kerf 16 has been formed in the slab 14, the kerf 16, having an outer radius, $R_1$, surrounds and defines a cylindrical sample 12 of the metal having an outer radius $R_2$. Because the kerf 16 generally borders the cylindrical sample, the radius, $R_2$, of the cylindrical sample 12 will generally be equal to an inner radius of the annular kerf 16. When the kerf 16 is made into the end of a slab 14, the sample 12 is attached to the slab of metal 14 along the back of the kerf 16 at the plane P.

Figure 2:
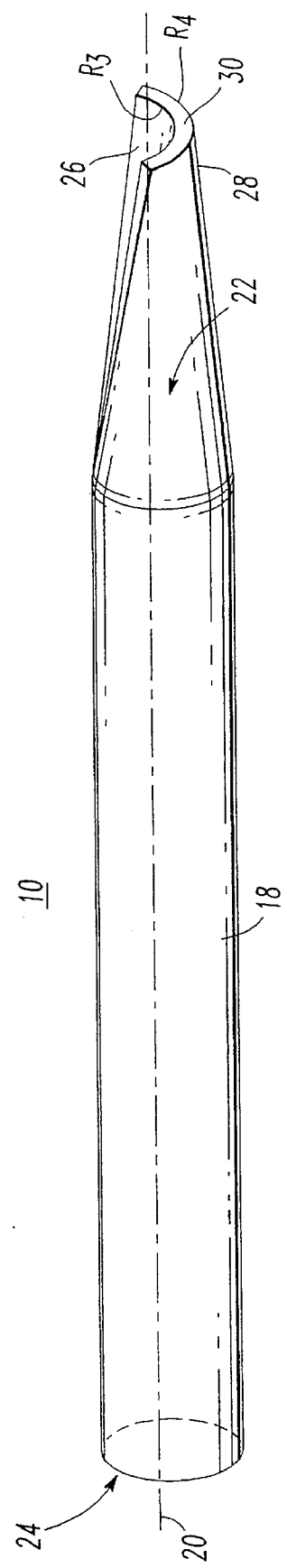
FIG. 2 is a perspective view of the preferred sample-extracting tool.

A sample extracting tool 10 shown in FIG. 2 is then utilized. The sample extracting tool 10 has a rigid elongated shaft 18. The shaft 18 has a longitudinal axis (depicted as dotted line 20 in FIG. 2) running along the length. The shaft 18 further has a first end 22 and a second end 24 located on opposite ends of the shaft 18. The first shaft end 22 has a cylindrical, concave inner surface 26 having a radius, $R_3$, and has a cylindrical, convex outer surface 28, having a radius, $R_4$.

The shaft first end 22 is tapered, therefore, the inner cylindrical surface 26 and the outer cylindrical surface 28 of the first end 22 lie at a desired angle relative to one another and converge so as to terminate in an arcuate edge 30. The first end 22 of the shaft 18 is sized and configured to fit within the kerf 16. The arcuate edge 30 of the first end 22 is preferably truncated, such as by being rounded or radiused. The truncated edge 30 of the tool has a thickness. The angle of taper of the first end and the amount that the first end is truncated determine the thickness of the edge 30. The thickness of the truncated edge 30 is configured so as no be less than the radial distance between the cylindrical sample and the outer radius of the kerf ($R_1-R_2$). The second end 24 of the shaft 18 is sized and configured to receive an impact thereto.

Figure 3:
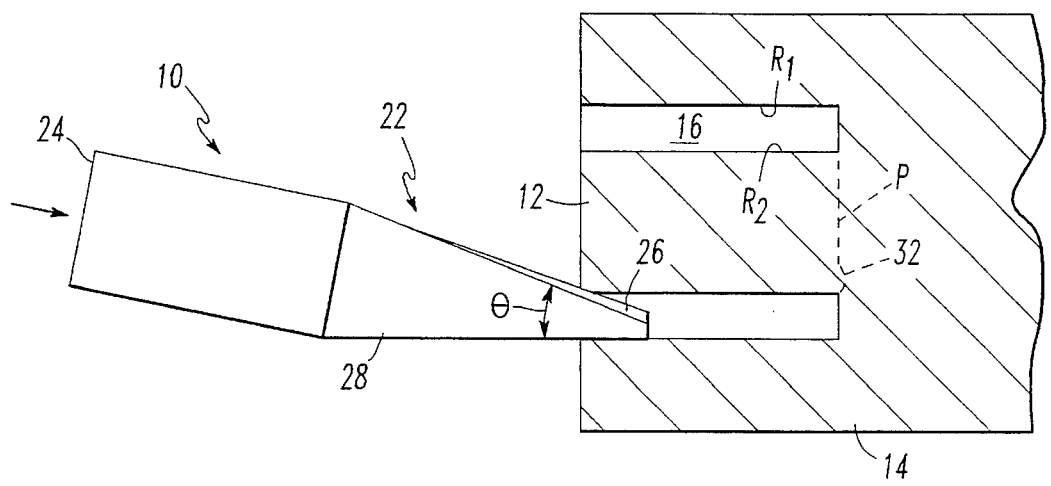
FIG. 3 is a cross sectional view of the sample-extracting tool inserted in an annular kerf of a steel slab.

Referring next to FIG. 3, the arcuate edge 30 of the tool 10 is inserted into the kerf 16. The tool 10 is oriented such that the inner concave cylindrical surface 26 lies adjacent the cylindrical sample 12 when the first end 22 of the tool 10 is inserted into the annular kerf 16. The radius, $R_3$, of the concave inner cylindrical surface 26 is greater than or equal to the radius, $R_2$, of the sample 12.

A force or impact such as a hammer blow (depicted as a bold arrow in FIG. 3) is administered to the second end 24 of the shaft 18 generally along the longitudinal axis 20 of the shaft 18. This impact causes the tool 10 to be driven deeper into the annular kerf 16. The widening contours of the tapered first end 22 of the tool 10 contact the portions of the slab 14 and sample 12 on either side of the kerf 16. Thus, a wedging force is transmitted from the outer surface 28 of the first end 22 to the portion of slab 14 surrounding the kerf 16 in contact with the tool outer surface 28. Similarly, a force is transmitted from the inner surface 26 of the first end 22 of the tool 10 to the sample 12. As this wedging force is transmitted from the inner surface 26 of the tool first end 22 to the sample 12, stress is built up along the bottom of the kerf 16 where the sample 12 is connected to the remainder of the metal slab 14. The stress buildup along the bottom of the kerf 16 causes a fracture 32 of the steel where the sample 12 is attached to the remainder of the slab 14. The fracture 32 extends across the entire width of the sample 12 allowing the sample 12 to be detached from the remainder of the slab 14 along the stress fracture 32. Thus, a generally cylindrical sample 12 is obtained, permitting testing of the steel beyond the flame altered area of the slab 14 without creating unnecessary material waste.

The tool 10 is preferably fabricated from steel. The inner cylindrical surface 26 has a radius, $R_3$, and the outer cylindrical surface has a radius, $R_4$. Preferably, the radius of the inner cylindrical surface is substantially the same as the radius of the outer cylindrical surface. The length of the shaft, the angle of taper between the upper and lower cylindrical surfaces, the thickness of the shaft and the radii of the inner and outer cylindrical surface may each be selected based upon the desired size of the sample to be extracted and the width and depth of the kerf. The inner cylindrical surface 26 and the outer cylindrical surface 28 of the first end 22 of the shaft 18 may thus be an any convenient angle θ, but a preferred embodiment lies at an angle θ of between 15° and 40° relative to one another.

For example, in a preferred embodiment, to extract a sample 12 having a diameter of approximately 1 inch and a depth of 1 inch, the radius, $R_3$, of the inner cylindrical surface 26 is approximately ½ inch (or slightly larger). Similarly, the radius, $R_4$, of the outer cylindrical surface 28 is also approximately ½ inch. The shaft diameter in this example may be approximately ¾ inch, with the overall length of the shaft being between 6½ and 7 inches. The preferred angle θ between the inner cylindrical surface and outer cylindrical surface 26, 28 is approximately 25°. Preferably, the arcuate edge 30 is blunted when the distance between the inner surface and the outer surface is approximately between 1/16 inch and 1/8 inch. With the edge 30 thus blunted and the angle of taper of the first end 22 thus selected, the edge 30 of the tool 10 will have a thickness that is less than the difference between the outer radius of the kerf, $R_1$, and the radius of the sample, $R_2$.

While certain present preferred embodiments have been shown and described, it is distinctly understood that the invention is not limited thereto but may be otherwise embodied within the scope of the following claims.

I claim:

1. A method of sampling a section of a metal object, comprising the steps of:

forming an annular kerf of outer radius $R_1$ upon said section of metal, such that an annular cavity surrounds a cylindrical sample of metal;

said sample having an outer radius $R_2$;

inserting into said kerf a tool having a rigid elongated shaft with a longitudinal axis and said shaft having a first end; said first end having a cylindrical, concave inner surface with a radius $R_3$, said first end having a cylindrical convex outer surface with a radius $R_4$, said inner and outer surfaces lying at an angle relative to one another such that said first end of said shaft is tapered and said first end of said shaft terminates in an arcuate edge;

urging said arcuate edge of said tool into said annular cavity such that said inner cylindrical surface is forcibly engaging said radius $R_2$ of said sample and said outer cylindrical surface is forcibly engaging said radius $R_1$ of said kerf;

administering a longitudinally-directed force upon a second end of said shaft until said cylindrical sample is separated from said section of metal; and removing said sample from said cavity.

2. The method of claim 1 wherein said annular kerf is formed through the use of a cylindrical hole cutting saw.

3. The method of claim 1 wherein said concave inner cylindrical surface radius $R_3$ is at least as large as said outer radius $R_2$ of said sample, 4. The method of claim 3 wherein said inner and outer cylindrical surfaces lie at an angle relative to one another of between 15° and 40°.

* * * * *